United States Patent
Wagner et al.

(10) Patent No.: US 6,719,759 B2
(45) Date of Patent: Apr. 13, 2004

(54) BONE PLATE

(75) Inventors: Michael Wagner, Vienna (AT); Robert Frigg, Bettlach (CH); Robert Schavan, Willich Anrath (DE)

(73) Assignees: Synthes AG Chur, Chur (CH); Synthes (USA), Paoli, PA (US)

( * ) Notice: Subject to any disclaimer, the term of this patent is extended or adjusted under 35 U.S.C. 154(b) by 33 days.

(21) Appl. No.: 09/946,974

(22) Filed: Sep. 6, 2001

(65) Prior Publication Data

US 2002/0045901 A1 Apr. 18, 2002

Related U.S. Application Data

(63) Continuation-in-part of application No. PCT/CH99/00106, filed on Mar. 9, 1999, and a continuation-in-part of application No. PCT/CH99/00107, filed on Mar. 9, 1999.

(51) Int. Cl.⁷ ............................................... A61B 17/80
(52) U.S. Cl. ...................................................... 606/69
(58) Field of Search .......................... 606/60, 69–71, 606/61

(56) References Cited

U.S. PATENT DOCUMENTS

| | | | |
|---|---|---|---|
| 3,552,389 A | 1/1971 | Allgower et al. | |
| 3,668,972 A | 6/1972 | Allgower et al. | |
| 3,716,050 A | 2/1973 | Johnston | |
| 3,779,240 A | 12/1973 | Kondo | |
| RE28,841 E | 6/1976 | Allgower et al. | |
| 4,219,015 A | 8/1980 | Steinemann | |
| 4,408,601 A | 10/1983 | Wenk | |
| RE31,628 E | 7/1984 | Allgower et al. | |
| 4,493,317 A | 1/1985 | Klaue | |
| 4,513,744 A | 4/1985 | Klaue | |
| 4,927,421 A | 5/1990 | Goble et al. | 606/73 |
| 4,957,497 A * | 9/1990 | Hoogland et al. | 606/71 |
| 5,002,544 A | 3/1991 | Klaue et al. | 606/69 |
| 5,006,120 A | 4/1991 | Carter | 606/69 |
| 5,304,180 A | 4/1994 | Slocum | 606/69 |
| 5,601,553 A | 2/1997 | Trebing et al. | 606/61 |
| 5,702,399 A | 12/1997 | Kilpela et al. | 606/72 |
| 5,709,686 A | 1/1998 | Talos et al. | 606/69 |
| 5,810,823 A | 9/1998 | Klaue et al. | 606/69 |
| 5,938,664 A | 8/1999 | Winquist et al. | 606/69 |
| 6,183,475 B1 | 2/2001 | Lester et al. | 606/69 |
| 6,206,881 B1 * | 3/2001 | Frigg et al. | 606/69 |

FOREIGN PATENT DOCUMENTS

| | | | |
|---|---|---|---|
| CH | 611147 | 5/1979 | ........... A61B/17/18 |
| DE | 43 41 980 A | 6/1995 | |
| DE | 43 43 117 A | 6/1995 | |
| DE | 4438264 A1 | 3/1996 | ........... A61B/17/70 |
| EP | 0 207 884 A2 | 1/1987 | ........... A61B/17/58 |
| WO | WO 97/09000 | 3/1997 | |

* cited by examiner

*Primary Examiner*—Kevin Shaver
*Assistant Examiner*—Michael B. Priddy
(74) *Attorney, Agent, or Firm*—Jones Day

(57) ABSTRACT

A bone plate includes an upper surface, a bone contacting surface, and at least one hole extending through the upper and bone contacting surfaces. The bone plate defines a longitudinal axis. The at least one hole defines a central axis and is elongated in a direction substantially aligned with the longitudinal axis. The hole may include a threaded portion and a non-threaded portion, and the threaded portion may extend through an angle of between about 190° and about 280° with respect to the central axis.

39 Claims, 4 Drawing Sheets

BONE PLATE

CROSS-REFERENCE To RELATED APPLICATIONS

The present application is a continuation-in-part of the U.S. National Stage designation of International Patent Application PCT/CH99/00106, filed Mar. 9, 1999 and the U.S. National Stage designation of International Patent Application PCT/CH99/00107, also filed Mar. 9, 1999. The entire content of both of these applications is expressly incorporated herein by reference thereto.

FIELD OF THE INVENTION

The present invention relates generally to devices for fixation of parts of a fractured bone and more specifically, to bone plates and systems for stabilization and/or compression of parts of a fractured bone.

BACKGROUND OF THE INVENTION

Bone plates may generally be utilized to carry out two different types of osteosynthesis, namely "rigid osteosynthesis" and "flexible osteosynthesis." Rigid osteosynthesis is used for medical care of joint fractures, simple shaft fractures (where nailing is impossible) as well as for osteotomies. Aside from the possibility of anatomical repositioning, the bone itself supports and stabilizes the osteosynthesis, which allows for the possibility of putting stress on the extremity earlier and without pain. Additional advantages of the medical care of stable fractures can be observed when the blood circulation in the bone is greatly diminished due to trauma. For treating "nonunions" or in the case of existing infection, the fracture must be kept stable in order to make bone healing possible and so as not to irritate the infection further by instability of the fracture gap.

Flexible osteosynthesis, also known as "biological osteosynthesis," may be desirable in the medical treatment of comminuted fractures in the shaft region of tubular bones. In the case of these fractures, it is an objective to maintain the proper length of the bone and to fix the bone ends joints) in their proper anatomic positions with respect to one another. With flexible osteosynthesis, the fracture zone is not directly affixed or manipulated, and consequently, the blood circulation in this area is not inhibited. Bone plates designed for flexible osteosynthesis thus operate similarly to a locking, intramedullary nail, which is anchored only in the metaphyses.

Since fractures cannot always be treated with one type of osteosynthesis, surgeons must frequently compromise because a bone plate, which allows him to combine the two types of osteosynthesis discussed above, is not available. Such a combination would be beneficial, for example, when a joint fracture can be compressed with traction screws through the bone plate and the whole of the joint may be connected to the diaphysis over an internal fixative with angularly stable screws. Another illustrative application concerns porotic bones, where a bone plate with axially and angularly stable screws can be anchored in the metaphysial fragment, with a stable plate-affixation being undertaken in the diaphyseal range with the assistance of a plate traction screw through the fracture. A primary fracture stabilization can be achieved by this type of procedure.

This situation has led to the development and marketing of bone implants for both types of osteosynthesis. The two types of implant group, however, are designed specifically for their respective method. Thus, the disadvantages of these two systems lies in the difficulty in combining them.

Thus, a need exists for improved bone plates that provide for both rigid and flexible osteosynthesis.

SUMMARY OF THE INVENTION

The present invention is directed to a bone plate that is adapted to be used for both rigid and flexible osteosynthesis, without compromising the plates ability to be used for either type of osteosynthesis. Accordingly, the bone plate of the present invention may be used as a compression plate or as an internal fixative.

According to one embodiment of the invention, the bone plate includes an upper surface, a bone contacting surface, and a plurality of holes extending through the upper and bone contacting surfaces. At least one of the holes is elongated in a direction substantially aligned with a longitudinal axis of the plate, and includes a threaded portion and a non-threaded portion. The threaded portion may extend over a range of greater than about 180° with respect to a central axis of the hole. The threaded portion of the hole is dimensioned and configured to engage a threaded head of a bone screw, and fix the bone screw at a predetermined angle with respect to the bone plate. Preferably, the threaded portion extends through the full thickness of the bone plate, i.e., from the upper surface to the bone contacting surface, thus maximizing the stability of the bone screw to bone plate interface.

With the threaded screw head fixed in the threaded portion of the elongated hole, the bone plate may be used as an internal fixative. Use in this configuration, however, creates high stresses at the interface of the bone plate and screw head because the plate is not forced against the bone, and therefore, the bone fracture is fixed primarily by friction between the plate and the bone. This increase in stress is taken into account by the threaded portion of the hole extending over a range of at least about 180° with respect to a central axis of the hole, and thereby enclosing the screw head in at least this angular range. This feature of the bone plate is especially advantageous where thin bone plates are involved. Preferably, the threaded portion is disposed on one of the two longitudinal ends of the hole. This positioning allows for the threaded portion to extend over a larger angular range. For example, the threaded portion may extend over a range of between about 190° and about 280°, and preferably over a range of between about 200° to 250°, thus maximizing the strength of the bone screw to bone plate interface.

According to another embodiment of the present invention, at least one of the holes may include a threaded portion that is angled or tapered with respect to a central axis of the hole. More specifically, the threaded portion may conically taper inward towards the bone-contacting surface of the bone plate. A bone screw to be rigidly fixed to the bone plate may include a threaded screw head that is tapered to substantially match the tapered shape of the threaded portion of the hole. Thus, the bone screw may be rigidly fixed to the bone plate by engagement between the matching conical threads. This method of attachment is especially advantageous when self-drilling screws are to be used since, due to the conical shape of the matching threads, the screw may be inserted into the bone independently of the plate. More specifically, the screw head becomes rigidly clamped to the plate only as the threaded screw head penetrates the threaded portion of the hole. Despite any initial misalignment between the threads on the screw head (the position of which are initially dictated by the orientation of the bone screw in the bone) and the threads on the bone plate, the conical shape of the mating threads ensures that the threads on the screw head will ultimately align with the threaded portion of the hole. When the conical thread screw head is tightened into the threaded portion of the hole, the screw head creates radial forces in the plate hole. Thus, the bone plate must be dimensioned and configured to withstand these high radial forces, e.g., to withstand flexing of the walls of the screw holes in the bone plate.

The threaded portion preferably tapers at a cone angle of between about 5° and about 20°. Preferably, the thread tapers at a cone angle of about 10°.

In the case where the threaded portion of the hole is tapered, as discussed above, the threaded portion may extend through a different angle when measured at the upper surface than when measured at the bone-contacting surface. For example, when measured at the upper surface, the threaded portion may extend through a first angle of between about 200° and about 270°, while when measured at the bone-contacting surface, the threaded portion may extend through a second angle of between about 180° and about 230°.

According to another aspect of the present invention, at least one of the holes may be dimensioned and configured to receive a ball shaped head of a bone screw and provide for compression of two fractured bone fragments. For example, according to one embodiment, the non-threaded portion of the elongated hole, discussed above, may include a concave, substantially spherical recess at the upper surface. The recess may be dimensioned and configured to accommodate the spherical head of a conventional bone screw. Such an arrangement may be especially useful when the bone screw is put in place eccentrically with respect to the hole, as is necessary for attaining compression of a fracture. Additionally, the non-threaded portion of the hole may flare outward in the area of the bone contacting surface to provide for increased angulation of the bone screw with respect to the bone plate.

The threaded portion of the hole may be positioned closer to the end of the elongated hole that is closer to the center of the plate, thus avoiding any undesirable effects on the compression capability of the non-threaded portion. Thus, when the bone plate is used as a compression plate, the geometry of the non-threaded portion (compression portion) is not adversely affected by the presence of the threaded portion.

As discussed above, the hole may be elongated. Thus, the elongated hole may define first and second dimensions on the bone contacting surface, wherein the first dimension $D_L$ is substantially parallel to the longitudinal axis of the bone plate and the second dimension $D_Q$ is substantially perpendicular to the longitudinal axis. The ratio of $D_L/D_Q$ may be within the range of about 1.1 to 3, and preferably is in the range of about 1.1 to 1.5. This ratio follows from the combination of the threaded portion (locking portion) with the non-threaded portion (compression portion), which requires a clamping path for the screw head. This ration of $D_L/D_Q$ represents a preferred compromise between compression and plate weakening due to the presence of the hole.

According to another embodiment of the invention, the underside of the bone plate may be concave, thus allowing the plate to conform to the rounded cross-section of the tibia, femur, humerus, lower arm bone, and other bones with which the present invention may be used. The concave configuration of the underside also allows a conventional bone screw to be inserted obliquely through the plate hole. This feature may be especially important when gripping a small bone fragment, which must be pulled up to the plate.

The present invention is also directed to a bone plating system including at least one bone screw having a screw head with a thread disposed thereon, the thread being configured and dimensioned to engage the threaded portion of the above-described bone plate holes. Preferably, the bone screw is self-tapping and/or self-drilling.

BRIEF DESCRIPTION OF THE DRAWINGS

To facilitate an understanding of the characteristics, structure and operation of the invention, preferred features of the invention are described in the accompanying discussion, wherein similar reference characters denote similar elements throughout the several views or embodiments, and wherein.

DETAILED DESCRIPTION OF THE PREFERRED EMBODIMENTS

Figure 1:
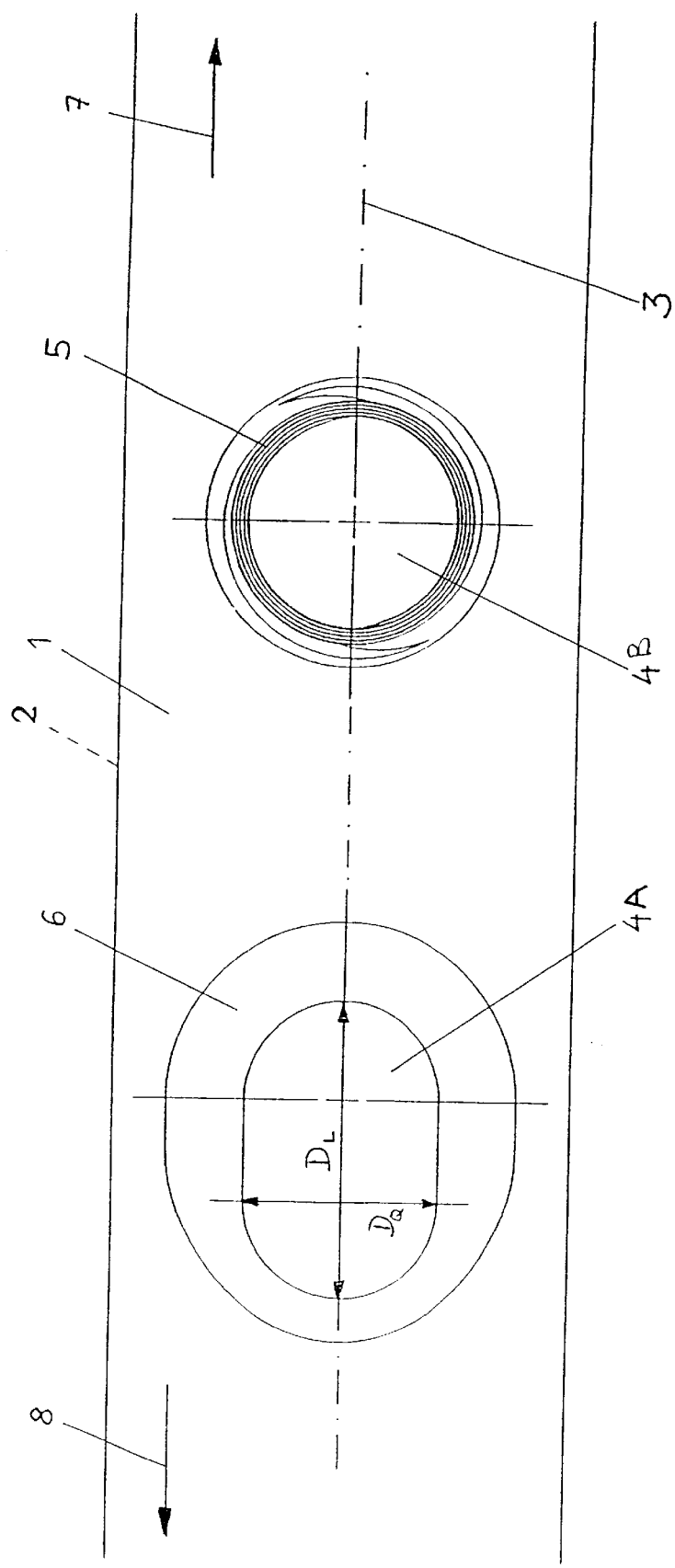
FIG. 1 is a top view of a segment of a bone plate according to one embodiment of the present invention.

One embodiment of a bone plate according to the present invention is shown in FIG. 1. The bone plate includes an upper surface 1, a bone-contacting surface 2, and defines a longitudinal axis 3. The bone plate further includes two holes 4A and 4B, which are generally located along the longitudinal axis 3, and extend through the bone plate from upper surface 1 to bone-contacting surface 2. Holes 4A and 4B are dimensioned and configured to receive the heads of bone screws. As shown in FIG. 1, arrow 7 indicates a longitudinal direction toward one end of the bone plate and arrow 8 indicates a longitudinal direction toward a central portion of the bone plate.

Still referring to FIG. 1, hole 4A, which is located closer to the central portion of the bone plate, is elongated along the longitudinal axis 3 of the bone plate. More specifically, hole 4A defines first and second dimensions on bone-contacting surface 2. First dimension $D_L$ is substantially parallel to longitudinal axis 3, and second dimension $D_Q$ is substantially perpendicular to longitudinal axis 3. First dimension $D_L$ is preferably larger than second dimension $D_Q$. According to one preferred embodiment, $D_L$ is 5.2 mm and $D_Q$ is 3 mm, however other dimensions are possible. Elongated hole 4A may be provided with a concave and preferably spherical recess 6 near upper surface 1. Recess 6 may be dimensioned to receive a bone screw having a substantially spherical-shaped head.

Figure 3:
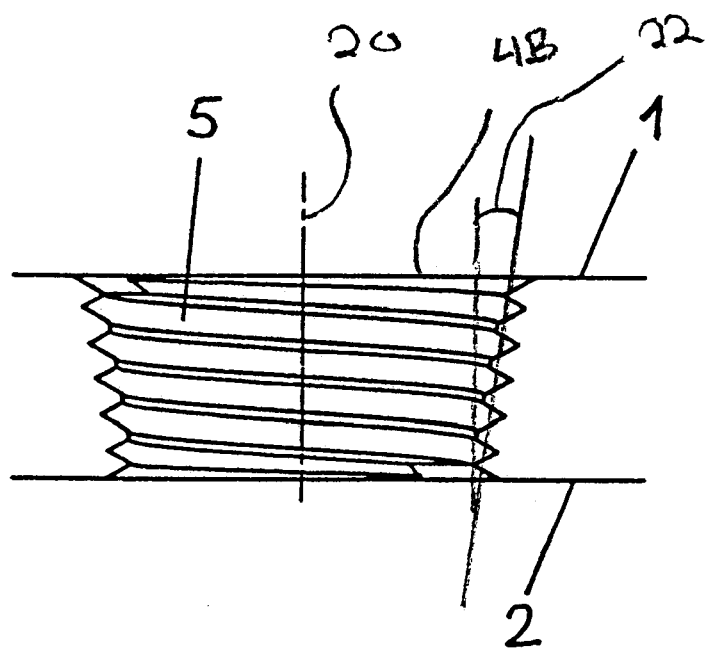
FIG. 3 is a longitudinal cross-sectional view showing a threaded hole of the bone plate of FIG. 1.

Hole 4B, which is located closer to one end of the bone plate, includes a thread 5 which extends through an angle of 360° around the hole 4B. As shown in the schematical representation of FIG. 1, hole 4B assumes the shape of a cone tapering inward in a direction toward bone contacting surface 2, and accordingly thread 5 also tapers inward toward bone contacting surface 2. As shown in FIG. 3, hole 4B and thread 5 preferably taper inward with respect to central axis 20 of hole 4B by a cone angle 22 of about 10°, however other value of cone angle 22 are possible. In addition, thread 5 is preferably a double thread. As shown in FIG. 3, thread 5 of hole 4B may run along the full thickness of the bone plate from the upper surface 1 to the bone-contacting surface 2.

Figure 2:
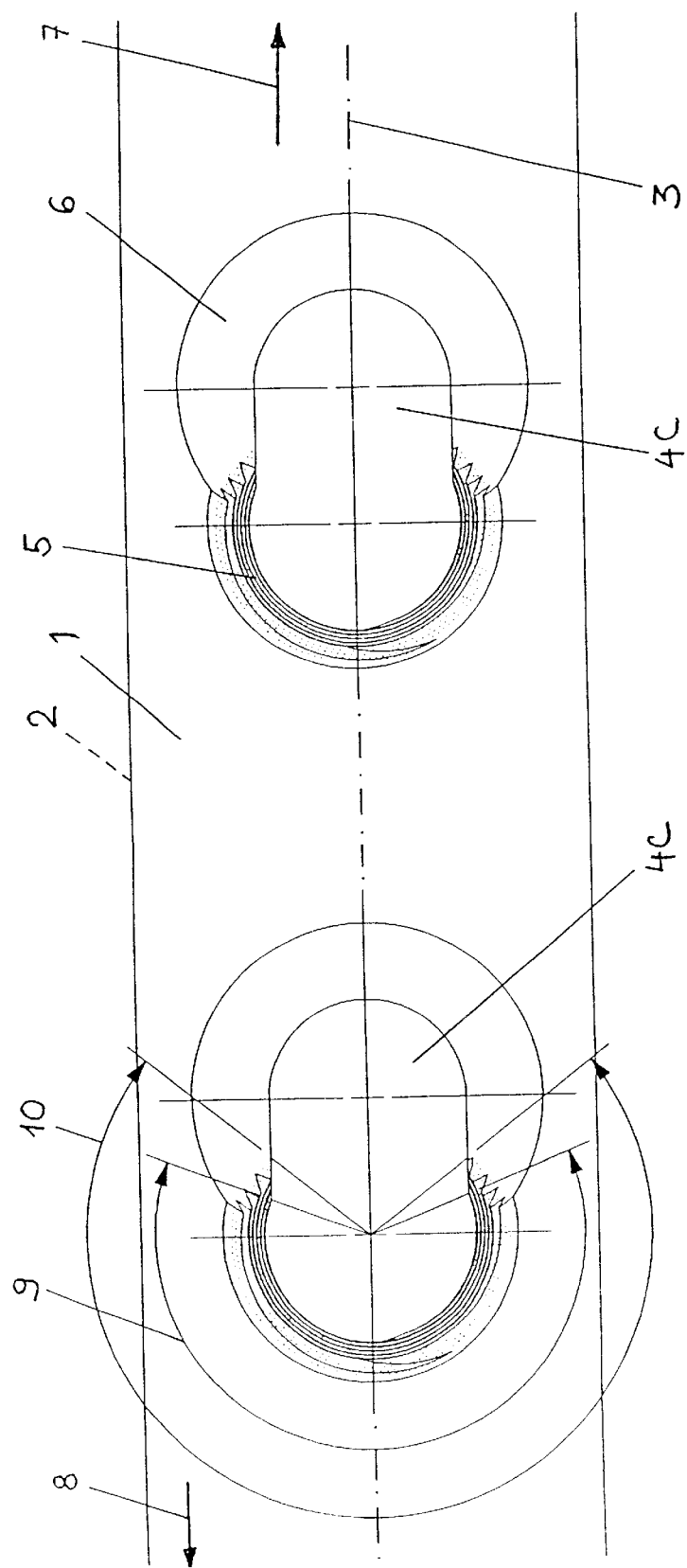
FIG. 2 is a top view of a segment of a bone plate according to another embodiment of the present invention.
Figure 4:
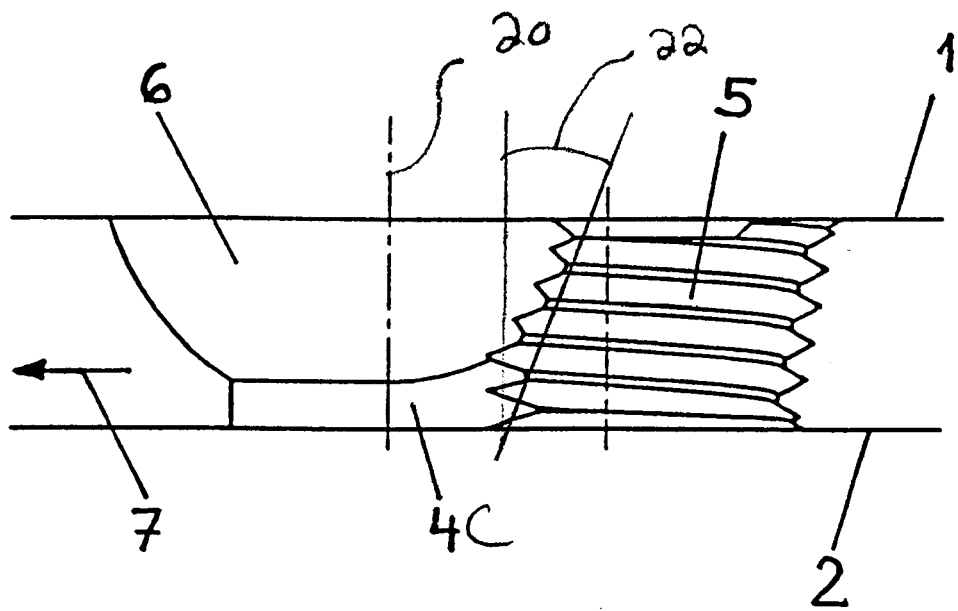
FIG. 4 is a longitudinal cross-sectional view of a partially-threaded, elongated hole of the bone plate of FIG. 2.

In one preferred embodiment of the invention shown in FIGS. 2 and 4, the two bone-plate holes 4A and 4B of FIG. 1 may be combined to form a combination hole 4C. The combination hole 4C is thus provided with a threaded portion which includes a thread 5, and a non-threaded portion which has no threads disposed thereon. The threaded portion is preferably located at the end of the hole 4C which is nearer to the central portion of the bone plate.

With reference to FIG. 2, when measured at upper surface 1, the threaded portion (thread 5) extends over a first angle 9 with respect to the central axis of hole 4C, and when measured at bone-contacting surface 2, the threaded portion (thread 5) extends over a second angle 10 with respect to the central axis. Preferably, first angle 9 is about 223° and second angle 10 is about 256°, however other values of first and second angles 9, 10 are possible.

The table below displays, for illustrative purposes only, preferred parameters which may be used depending on the diameter of thread 5.

| Thread Diameter | 3.0 mm | 4.0 mm | 5.0 mm |
|---|---|---|---|
| Double Thread | yes | yes | yes |
| Thread Pitch | 0.7 mm | 0.9 mm | 1.0 mm |
| Thread Depth (measured as ½ of outside/inside diameter-differential) | 0.2025 mm | 0.2575 mm | 0.2810 mm |
| Angular Range (at upper surface) | 200° | 200° | 190° |
| Angular Range (at bone-contacting surface) | 260° | 240° | 250° |
| Shape of Threaded Portion | Conical | Conical | Conical |

Figure 5:
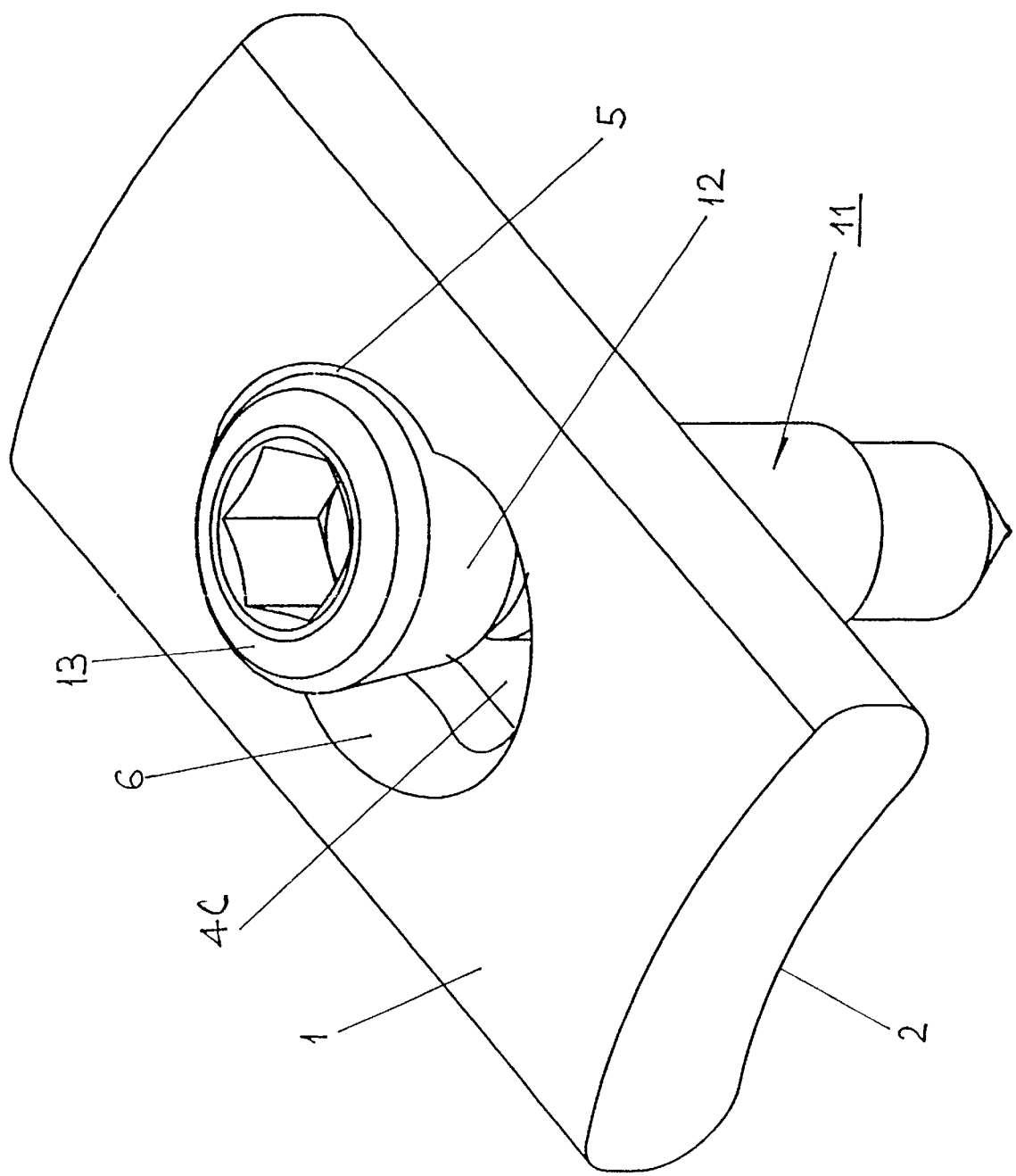
FIG. 5 is a perspective view of the segment of the bone plate of FIG. 2, with a bone screw inserted into the partially-threaded, elongated hole.

Referring to FIG. 5, combination hole 4C is shown with a bone screw 11 received therein. The bone screw preferably has a screw head 13 with a thread 12 disposed thereon. As shown in FIG. 5, thread 12 may substantially match thread 5 of combination hole 4C. Preferably, bone screw 12 is self-drilling and/or self-tapping.

While preferred embodiments and features of the present invention have been disclosed herein, it will be appreciated that numerous modifications and embodiments may be devised by those skilled in the art. It is intended that the appended claims cover all such modifications and embodiments as fall within the true spirit and scope of such claims and that the claims not be limited to or by such preferred embodiments or features.

What is claimed:

1. A bone plate defining a longitudinal axis and comprising:
   an upper surface;
   a lower surface; and
   at least one hole extending through the upper and lower surfaces, the hole defining a central axis and being elongated in a direction substantially aligned with the longitudinal axis, wherein the hole is at least partially threaded and the threaded portion of the hole tapers inward with respect to the central axis.

2. The bone plate of claim 1, wherein the threaded portion conically tapers inward in a direction along the central axis from the upper surface towards the lower surface.

3. The bone plate of claim 1, wherein the threaded portion tapers inward with respect to the central axis by a cone angle of between about 5° and about 20°.

4. The bone plate of claim 3, wherein the threaded portion conically tapers from the upper surface to the lower surface.

5. The bone plate of claim 1, wherein:
   the hole defines a first dimension on the lower surface that is substantially parallel to the longitudinal axis;
   the hole defines a second dimension on the lower surface that is substantially perpendicular to the longitudinal axis; and
   the first dimension is between 1.1 and 3 times larger than the second dimension.

6. The bone plate of claim 1, further comprising a bone screw including a screw head that is configured and dimensioned to threadably engage the threaded portion and fix the bone screw at a predetermined angle with respect to the bone plate.

7. The bone plate of claim 1, wherein the hole is configured and dimensioned to engage a substantially spherical screw head and provide compression of fractured bone fragments.

8. The bone plate of claim 7, wherein the hole includes a non-threaded portion having a concave recessed portion in the upper surface.

9. The bone plate of claim 8, wherein the recessed portion is substantially spherical.

10. The bone plate of claim 1, wherein the threaded portion extends through an angle of between about 190° and about 280° with respect to the central axis.

11. The bone plate of claim 1, wherein the threaded portion extends through an angle of between about 200° and about 250° with respect to the central axis.

12. The bone plate of claim 1, further comprising at least one second hole that is at least partially threaded, wherein the second hole tapers inward in a direction along the central axis from the upper surface to the lower surface.

13. The bone plate of claim 12, wherein the second hole defines an outer perimeter that is substantially circular.

14. A bone plate defining a longitudinal axis and comprising:
   an upper surface;
   a lower surface;
   a first hole extending through the upper and lower surfaces, the first hole defining a central axis and being elongated in a direction substantially aligned with the longitudinal axis, wherein the first hole is at least partially threaded; and
   a second hole extending through the upper and lower surfaces and defining a central axis, the second hole being at least partially threaded, and tapering inward in a direction along the central axis from the upper surface to the lower surface.

15. The bone plate of claim 14, wherein the first hole includes a recessed portion near the upper surface.

16. The bone plate of claim 15, wherein the recessed portion is substantially concave.

17. The bone plate of claim 16, wherein the recessed portion is substantially spherical.

18. The bone plate of claim 14, wherein the first hole defines an outer perimeter, at least a portion of which tapers inward from the upper surface to the lower surface.

19. The bone plate of claim 18, wherein the tapered portion of the outer perimeter defines at least one ramp surface for engagement with a screw head.

20. The bone plate of claim 14, further comprising a bone screw including a substantially spherical screw head that is configured and dimensioned to engage the first hole for providing compression of fractured bone fragments.

21. The bone plate of claim 14, further comprising a bone screw including a screw head that is configured and dimensioned to threadably engage the threads on the first and second holes.

22. The bone plate of claim 21, wherein the screw head is tapered.

23. The bone plate of claim 14, wherein the second hole defines an outer perimeter that is substantially circular.

24. A bone plate defining a longitudinal axis and comprising:
   an upper surface;
   a lower surface; and
   at least one hole extending through the upper and lower surfaces, the hole defining a central axis and being elongated in a direction substantially aligned with the longitudinal axis, wherein the hole includes a threaded portion and a non-threaded portion, and the threaded portion extends through an angle of between about 190° and about 280° with respect to the central axis.

25. The bone plate of claim 24, wherein the threaded portion extends through an angle of between about 200° and about 250° with respect to the central axis.

26. The bone plate of claim 24, wherein:
   the threaded portion extends through a first angle at the upper surface;
   the threaded portion extends through a second angle at the lower surface; and
   the first angle is larger than the second angle.

27. The bone plate of claim 26, wherein the first angle is between about 200° and about 270°, and the second angle is between about 180° and about 230°.

28. The bone plate of claim 24, wherein the hole defines first and second ends spaced apart along the longitudinal axis, and the threaded portion is disposed adjacent one of the ends.

29. The bone plate of claim 28, wherein the threaded portion is located closer to a central portion of the bone plate than to an end portion of the bone plate.

30. The bone plate of claim 24, wherein the non-threaded portion is configured and dimensioned to engage a substantially spherical screw head and provide compression of fractured bone fragments.

31. The bone plate of claim 30, wherein the non-threaded portion includes a concave recessed portion in the upper surface.

32. The bone plate of claim 31, wherein the recessed portion is substantially spherical.

33. The bone plate of claim 24, wherein:
   the hole defines a first dimension on the lower surface that is substantially parallel to the longitudinal axis;
   the hole defines a second dimension on the lower surface that is substantially perpendicular to the longitudinal axis; and
   the first dimension is between 1.1 and 3 times larger than the second dimension.

34. The bone plate of claim 24, wherein the threaded portion tapers inward in a direction from the upper surface towards the lower surface.

35. The bone plate of claim 34, in the threaded portion conically tapers at a cone angle of between about 5° and about 20°.

36. The bone plate of claim 35, wherein the threaded portion conically tapers from the upper surface to the lower surface.

37. The bone plate of claim 24, further comprising a bone screw including a screw head that is configured and dimensioned to threadably engage the threaded portion and fix the bone screw at a predetermined angle with respect to the bone plate.

38. The bone plate of claim 24, further comprising at least one second hole that is at least partially threaded, wherein the second hole tapers inward in a direction along the central axis from the upper surface to the lower surface.

39. The bone plate of claim 38, wherein the second hole defines an outer perimeter that is substantially circular.

* * * * *